United States Patent

Matthews et al.

(10) Patent No.: US 6,714,831 B2
(45) Date of Patent: Mar. 30, 2004

(54) PAINT DEFECT AUTOMATED SEEK AND REPAIR ASSEMBLY AND METHOD

(75) Inventors: Thurston Sandy Matthews, Farmington Hills, MI (US); Gary David Farquhar, Farmington Hills, MI (US); Valerie Catherine Bolhouse, Northville, MI (US)

(73) Assignee: Ford Motor Company, Dearborn, MI (US)

( * ) Notice: Subject to any disclaimer, the term of this patent is extended or adjusted under 35 U.S.C. 154(b) by 0 days.

(21) Appl. No.: 09/683,612

(22) Filed: Jan. 24, 2002

(65) Prior Publication Data

US 2003/0139836 A1 Jul. 24, 2003

(51) Int. Cl.[7] .......................... G06F 19/00; G06K 9/00; G01N 21/00
(52) U.S. Cl. ................. 700/110; 700/117; 382/141; 356/237.2
(58) Field of Search .......................... 700/90, 95, 110, 700/117; 382/141; 356/237.1, 237.2

(56) References Cited

U.S. PATENT DOCUMENTS

| | | | | |
|---|---|---|---|---|
| 4,920,385 A | * | 4/1990 | Clarke et al. ............ 356/237.2 |
| 4,941,182 A | * | 7/1990 | Patel ..................... 382/141 |
| 5,394,654 A | | 3/1995 | Shimbara et al. ............ 451/6 |
| 5,477,268 A | * | 12/1995 | Shimbara et al. ........... 348/128 |
| 5,716,262 A | | 2/1998 | Kiba ..................... 451/103 |
| 5,844,801 A | | 12/1998 | Kodama et al. ............ 700/110 |
| 6,013,308 A | * | 1/2000 | Saito ..................... 427/8 |
| 6,320,654 B1 | * | 11/2001 | Alders et al. ............ 356/237.2 |

* cited by examiner

*Primary Examiner*—Leo Picard
*Assistant Examiner*—Ryan A. Jarrett
(74) *Attorney, Agent, or Firm*—Raymond L. Coppiellie; Artz & Artz

(57) ABSTRACT

A method of detecting and repairing paint defects on a vehicle body (10) is provided, including developing paint defect data using electronic imaging of the vehicle body (S1), referencing said electronic imaging with vehicle CAD data to develop three dimensional paint defect coordinates for each paint defect (S2), storing said paint defect data and said paint defect coordinates referenced to the vehicle body (S3), developing a repair strategy based upon said paint defect data and said paint defect coordinates (S4), and performing an automated repair on the paint defects based upon said repair strategy (S5).

8 Claims, 3 Drawing Sheets

PAINT DEFECT AUTOMATED SEEK AND REPAIR ASSEMBLY AND METHOD

BACKGROUND OF THE INVENTION

The present invention relates to a method and assembly for inspecting painted surfaces of a vehicle body, locating and tracking defects in the painted surface, and repairing such defects if necessary.

Automotive assembly plants are comprised of numerous individual assembly processes that must each be performed accurately and efficiently in order to produce a successful vehicle. Automation has proven highly successful in improving the accuracy and efficiency of many such individual operations by reducing incidents of operator error. One particular field in which mechanical automation has the potential to provide significant improvements over human operators is in the area of Human inspection can take considerable time and is prone to error. This runs counter to the driving forces of accuracy, efficiency, and cost effectiveness that guide the modern automotive assembly plant.

An assembly process that has proven to be particularly susceptible to operator error has been automotive paint operations. Often, a finished vehicle has undergone several paint processes prior to leaving the plant. Processes such as e-coat, prime, enamel, and clear coat can be applied to the vehicle in various combinations. Defects arising during any one of these operations may result in an unsatisfactory appearance of the vehicle. Although it is often possible to repair a defect arising out of one of these operations, it can be a significant task to locate these defects quickly and accurately and take such remedial action with minimal disruption to the automotive assembly processes. Moreover, these repair operations are relatively expensive and can be ineffective.

Human inspection and flagging of such defects has left considerable room for improvements in efficiency. Often defects must be immediately addressed or flagged (marked) by the inspectors such that the vehicle may be either removed from the production line, or remedied prior to further painting processes. The inefficiencies of these operations have provided the driving force for automating the vehicle inspection and repair process. In this light, numerous automated optical inspection techniques have been developed. Although these optical techniques have proven successful in locating defects, they often provide inadequate procedures and insufficient information for remedying the defect. Often, operators are required to step in and perform remedial procedures prior to the vehicle advancing on the line. In other methods, the defect is visually marked such that operators further along the plant line must locate and address the defect. The application of automation to not only the inspection process, but also to the isolation and repair of defects, would provide considerable advancements and efficiency over these existing solutions.

One notable advancement in the field of vehicle inspection has been the use of CAD design information in conjunction with optical imaging to locate defects within the vehicle surfaces prior to paint operations. These systems can determine deviations in the structure from design data in order to insure that the surface is in proper form for paint application prior to typical spray booth operations. It would be highly desirable to advance this known technology in order to provide improvements within the paint assembly processes. In addition, it would be highly desirable to integrate this technology into an automated paint seek and repair assembly that could provide advancements in the accuracy, efficiency, and cost effectiveness of known paint operations.

SUMMARY OF THE INVENTION

It is, therefore, an object of the present invention to provide a method and assembly for automated inspection and locating of paint defects on a vehicle. It is a further object of the present invention to provide automated paint defect repair in response to the located paint defects.

In accordance with those and the other objects of the present invention, a method of detecting and repairing paint defects on a vehicle body is provided. The method includes developing paint defect data using electronic imaging of the vehicle body. The electronic imaging is referenced with vehicle CAD data to develop three dimensional paint defect coordinates for each paint defect. The paint defect data and the paint defect coordinates are stored with reference to the vehicle body. A repair strategy is developed based upon the paint defect data and the paint defect coordinates. Finally, an automated repair is performed on the paint defects based upon the repair strategy.

Other objects and features of the present invention will become apparent when viewed in light of the detailed description of the preferred embodiment when taken in conjunction with the attached drawings and appended claims.

DETAILED DESCRIPTION

Figure 1:
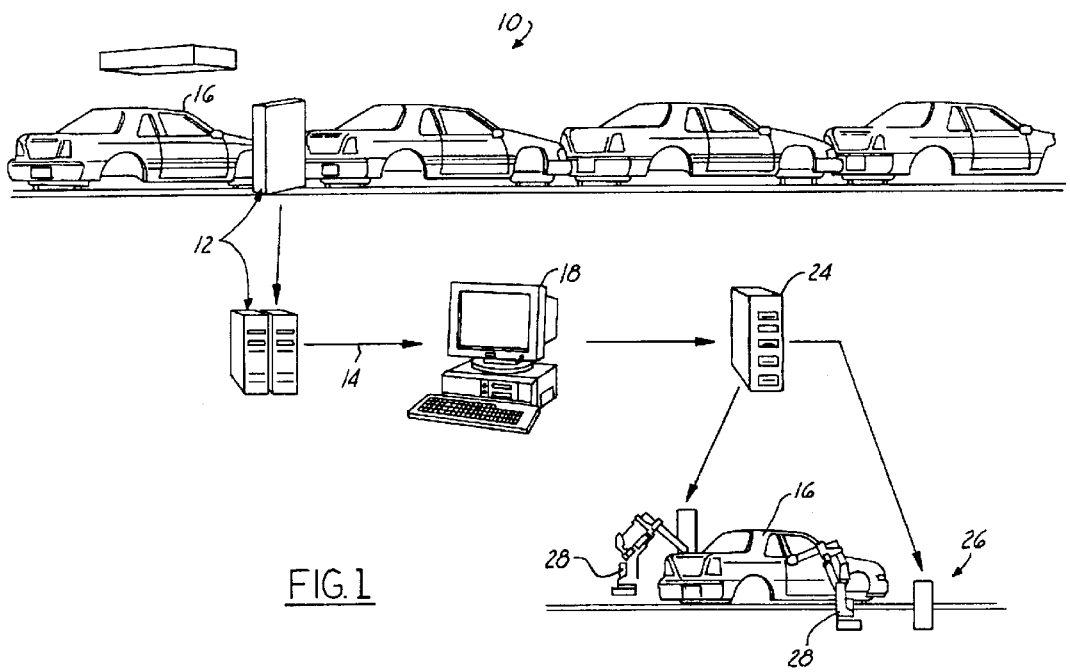
FIG. 1 is a schematic view of an embodiment of an automated paint seek and repair system in accordance with the present invention.
Figure 2:
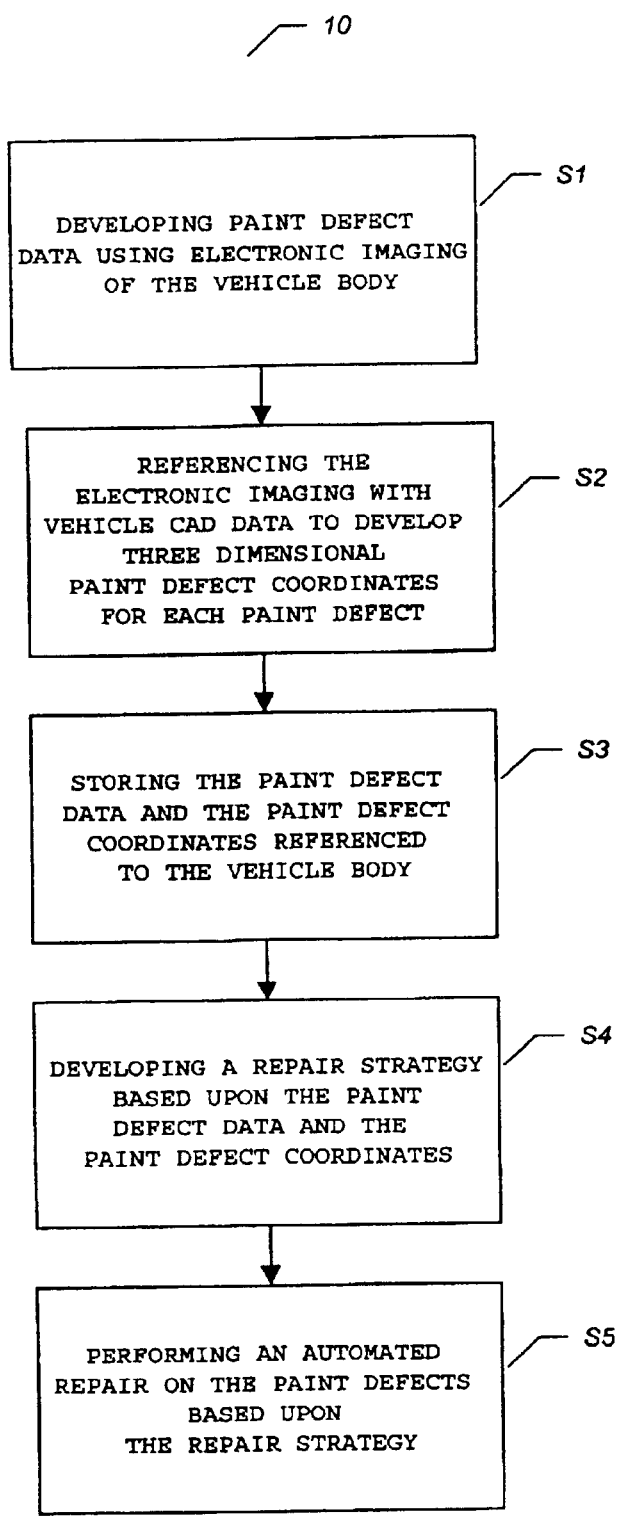
FIG. 2 is a flow chart of an operation sequence of the automated paint seek and repair system shown in FIG. 1.

FIG. 1 illustrates a schematic view of an embodiment of an assembly for automated paint defect detection and repair on a vehicle body 10 according to the present invention. An operational sequence of the assembly for automated defect detection and repair 10 is described in FIG. 2. The assembly 10 is intended to identify and repair paint defects after a variety of paint processes. In a typical automotive paint assembly, this may constitute inspection after e-coat, prime, and final paint applications. It should be understood, however, that the assembly 10 may be widely applicable to a variety of paint application systems, including non-automotive paint application systems.

The assembly 10 includes an imaging system 12. The imaging system 12 generates paint defect data 14 by electronically imaging the vehicle body, as generally indicated by identifier S1. Imaging systems 12, such as vision scanners are well known in the automotive industry. Although it is contemplated that a variety of imaging systems 12 may be used by the present invention, one embodiment contemplates the use of an optical system, such as a vision scanner with telecentric optics. The imaging system 12 generates paint defect data 14 as it scans the vehicle body 16. Although it is contemplated that paint defect data 14 may encompass a wide variety of paint defect attributes, in one embodiment, the paint defect data includes the size, type and location of a paint defect.

Figures 3A, 3B:
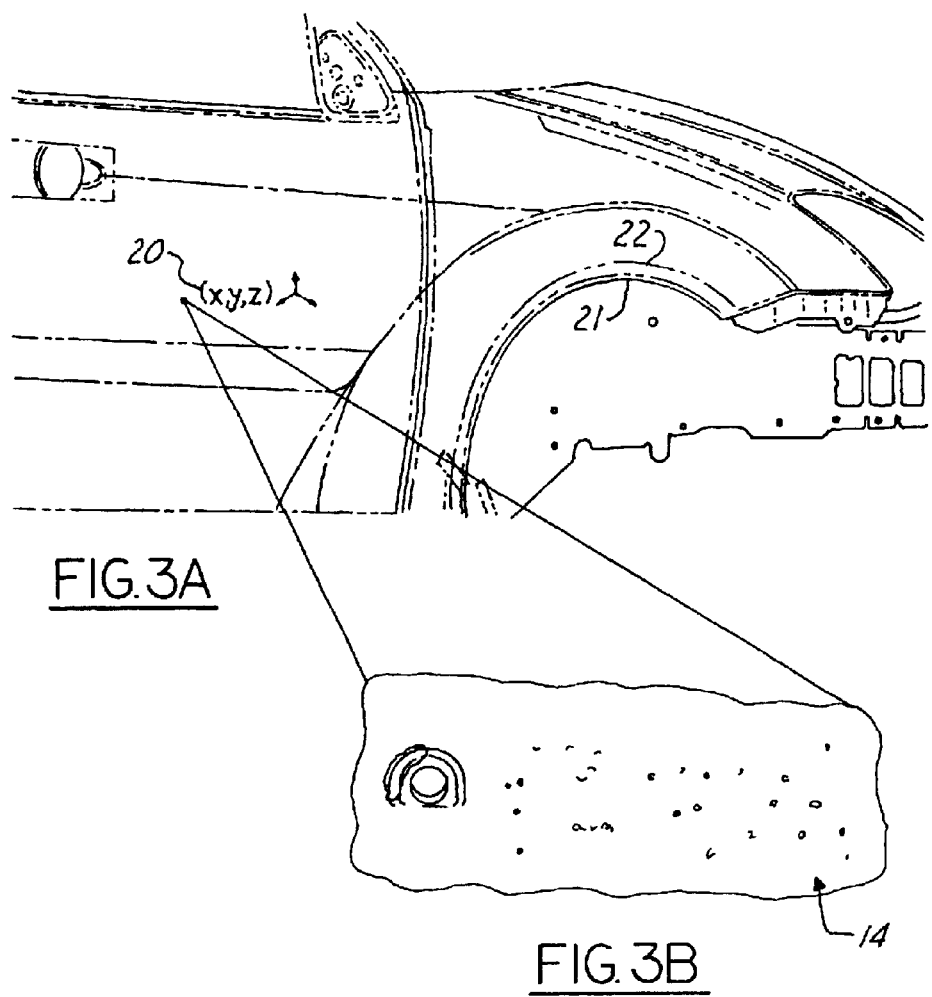
FIG. 3A is an illustration of the referencing electronic imaging with CAD data utilized by the present invention.
FIG. 3B is a detailed illustration of the referencing electronic imaging with CAD data illustrated in FIG. 3A, the detail illustrating a paint defect.

The paint defect data 14 is passed on to a vision cell controller 18. The vision cell controller 18 receives the information from the imaging system 12. The vision cell controller 18 references the information from the imaging system 12 with vehicle CAD data to develop three dimensional paint defect coordinates 20 for each paint defect as generally indicated by identifier S2. The advantage of this process is that all geometric dimensions are calibrated from a CAD master coordinates and thereby provides improved accuracy over many present systems. A representation of the reference of imaging information 21 to CAD data 22 is illustrated in FIG. 3A. A detail of a paint defect is illustrated in FIG. 3B. The vision cell controller 18 provides x, y, z and surface normal data. This not only provides improved accuracy, but allows for improved defect location such that defects need not be immediately addressed, but can be accurately located any time or position later in the process as the vehicle body 16 continues down the assembly line, or is transferred to a repair station. In addition, the vision controller 18 can be utilized to sort paint defects based upon size, type and location.

The vision cell controller 18 also stores the paint defect data 14 and the paint defect coordinates 20 referenced to the vehicle body 16 as generally indicated by identifier S3. Referencing the paint defect coordinates 20 to the vehicle body 16 further serves to dissociate the inspection from the repair time. This distancing allows the repair to be accomplished remote from the imaging. In one embodiment, the storage is accomplished through the use of a database containing the defect table. In alternate embodiments, however, the defect data 14 can be referenced to the vehicle body 16 in a variety of fashions including, but not limited to, storage of the data within portable memory affixed to the vehicle body 16 or the sled transporting it on the assembly line. In addition, the vision cell controller 18 can be utilized as the primary interface to the operator for identification of defect locations. Further, the vision cell controller 18 can provide setup functions, and can provide calibration functions for the imaging system 12 and any robotic controls. Inspection and repair masks can be automatically generated from the CAD geometry with precise tolerances around edges and character lines. It should be understood, that it is possible for different or additional systems to be used in conjunction with the vision cell controller 18 to provide these functions as well as a variety of others. Although a single controlled system may be utilized to accomplish the present invention, the modular system described provides a solution that can be easily implemented into existing facilities and can allow for more efficient placement of equipment within a line layout.

The assembly 10 further includes a robot cell controller 24. The robot cell controller 24 develops a repair strategy based upon the paint defect data and the paint defect coordinates as generally indicated by identifier S4. The repair strategy may be based on a variety of known approaches toward paint defect repair. This may include path and processing parameters, tools, and robot choice. In addition, the robot cell controller 24 can be assigned a variety of additional tasks in order to improve the operation and functionality of the assembly 10. These additional tasks may include, but are not limited to, generating robot paths and tooling parameters, performing quality data logging, and error reporting. In addition, the robot cell controller 24 can be utilized as an operator's primary interface for repair operation, directing and controlling the robots.

The assembly 10 also includes an automated robotic repair system 26. The automated robotic repair system 26 performs an automated repair on the paint defects based upon the repair strategy, as generally indicated by identifier S5. It is contemplated that the robotic repair system 26 may include a wide variety of automated robots 28 suited for the repair of a wide variety of paint defects. These automated robots 28 are envisioned to accomplish a variety of tasks including sanding and polishing the paint defect. Other treatments, particularly suited to a given size or type of paint defect are contemplated. One advantage of the present invention is that the automated robot 28 can be programmed to approach the surface of the vehicle body 16 along the normal vector to ensure even forces across the sanding pad or other tool. This provides the benefit of creating a more even treatment of the paint defect, and can be important for certain treatments such as feathering. Additionally, as mentioned, inspection and repair masks can be automatically generated from the CAD geometry with precise tolerances around edges and character lines such that the treatment of the paint defect may be specialized for a given defect. It is also envisioned, that in at least one embodiment of the present invention, the automated repair system 26 can include force feedback sensors. This also provides a greater range of control over the repair processes. The use of force feedback sensors is well known within the robotics field.

Although specific embodiments and components have been referred to in the present specification, it should be understood that a wide variety of configurations may be utilized to practice the present invention. Specifically, the imaging system 12, the vision cell controller 18, the robot cell controller 24 and the robotic repair system 26 need not be individual self contained systems. These components can be in any combination to form single components accomplishing some or all of their tasks. In another embodiment, centralized computer control may be utilized while retaining separate mechanical components. While particular embodiments of the invention have been shown and described, numerous variations and alternative embodiments will occur to those skilled in the art. Accordingly, it is intended that the invention be limited only in terms of the appended claims.

What is claimed is:

1. A method of detecting and repairing paint defects on a vehicle body, comprising:

developing paint defect data using electronic imaging of the vehicle body;

referencing said electronic imaging with vehicle CAD data to develop three dimensional paint defect coordinates for each paint defect;

using said vehicle CAD data to determine a vehicle surface normal at each paint defect;

storing said paint defect data and said paint defect coordinates referenced to CAD master coordinates;

developing a repair strategy based upon said paint defect data and said paint defect coordinates; and performing an automated repair on the paint defects relative to their said vehicle surface normals.

2. A method of detecting and repairing paint defects on a vehicle body as described in claim 1, wherein said electronic imaging includes the use of an optics scanner.

3. A method of detecting and repairing paint defects on a vehicle body as described in claim 1, wherein said storing includes the use of a paint defect database.

4. A method of detecting and repairing paint defects on a vehicle body as described in claim 1, wherein said paint defect data includes the size and location of said paint defects.

5. A method of detecting and repairing paint defects on a vehicle body as described in claim 1, wherein said referencing is accomplished through the use of a vision cell controller.

6. A method of detecting and repairing paint defects on a vehicle body as described in claim 1, further comprising:

generating robot paths for a plurality of automated robots using said repair strategy.

7. A method of detecting and repairing paint defects on a vehicle body as described in claim 6, wherein said performing an automated repair includes programming said plurality of automated robots to approach the vehicle body along a normal vector.

8. A method of detecting and repairing paint defects on a vehicle body as described in claim 1, further comprising:
utilizing force feedback to adjust said automated repair.

\* \* \* \* \*